United States Patent
Kim

(10) Patent No.: US 10,578,688 B2
(45) Date of Patent: Mar. 3, 2020

(54) METHOD AND APPARATUS FOR FILTERING MAGNETIC FIELD INDUCED IN COIL OF MRI SYSTEM

(71) Applicant: Samsung Electronics Co., Ltd., Suwon-si (KR)

(72) Inventor: Kyoungnam Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 275 days.

(21) Appl. No.: 15/503,594

(22) PCT Filed: Aug. 13, 2015

(86) PCT No.: PCT/KR2015/008513
§ 371 (c)(1),
(2) Date: Feb. 13, 2017

(87) PCT Pub. No.: WO2016/024839
PCT Pub. Date: Feb. 18, 2016

(65) Prior Publication Data
US 2017/0234949 A1     Aug. 17, 2017

(30) Foreign Application Priority Data
Aug. 13, 2014  (KR) .................. 10-2014-0105432

(51) Int. Cl.
*G01R 33/36* (2006.01)
*A61B 5/055* (2006.01)
*A61B 5/00* (2006.01)

(52) U.S. Cl.
CPC .......... *G01R 33/3657* (2013.01); *A61B 5/055* (2013.01); *G01R 33/3692* (2013.01); *A61B 5/721* (2013.01)

(58) Field of Classification Search
CPC .... A61B 5/055; A61B 5/721; G01R 33/3657; G01R 33/3692; G01R 33/36; G01R 33/3642
(Continued)

(56) References Cited

U.S. PATENT DOCUMENTS 5,355,885 A    10/1994  Tsuda et al.
6,144,205 A *  11/2000  Souza .................. G01R 33/341
                                                    324/322
(Continued)

FOREIGN PATENT DOCUMENTS

JP    2007-282735 A    11/2007
JP    2008-119249 A     5/2008
(Continued)

OTHER PUBLICATIONS

Yang, X., et al., "T/R Switched, Baluns, and Detuning Elements in MRI RF coil," ISMRM Fourteenth Scientic Meeting Weekend Syllabus, 2006 (7 pages).
(Continued)

*Primary Examiner* — Rishi R Patel
(74) *Attorney, Agent, or Firm* — NSIP Law

(57) ABSTRACT

Provided is a method and an apparatus for filtering a magnetic field induced in a coil of a magnetic resonance imaging (MRI) system. The method includes: applying an electromagnetic signal to an object, wherein the applying is performed by a transmit coil; while the electromagnetic signal is applied, emitting light toward a receive-only coil that obtains a magnetic resonance signal that is generated in the object due to the applied electromagnetic signal; and when the receive-only coil receives the emitted light, filtering a magnetic field induced in the receive-only coil due to the applied electromagnetic signal.

18 Claims, 4 Drawing Sheets

(58) Field of Classification Search
USPC .................................................. 324/300–322
See application file for complete search history.

(56) References Cited

U.S. PATENT DOCUMENTS

| | | | |
|---|---|---|---|
| 7,823,306 B1* | 11/2010 | Kersten | A61B 5/0046 |
| | | | 40/436 |
| 8,527,046 B2 | 9/2013 | Connelly et al. | |
| 2008/0204017 A1 | 8/2008 | Takamori et al. | |
| 2010/0277175 A1 | 11/2010 | Weiss | |
| 2012/0223709 A1* | 9/2012 | Schillak | G01R 33/3607 |
| | | | 324/309 |
| 2012/0223715 A1* | 9/2012 | Park | A61B 5/0035 |
| | | | 324/318 |
| 2014/0002085 A1 | 1/2014 | Biber et al. | |

FOREIGN PATENT DOCUMENTS

| | | |
|---|---|---|
| JP | 2008-229008 A | 10/2008 |
| WO | WO 03/026505 A1 | 4/2003 |

OTHER PUBLICATIONS

International Search Report issued in counterpart International Application No. PCT/KR2015/008513 dated Nov. 24, 2015 (3 pages).

* cited by examiner

[Fig. 1]
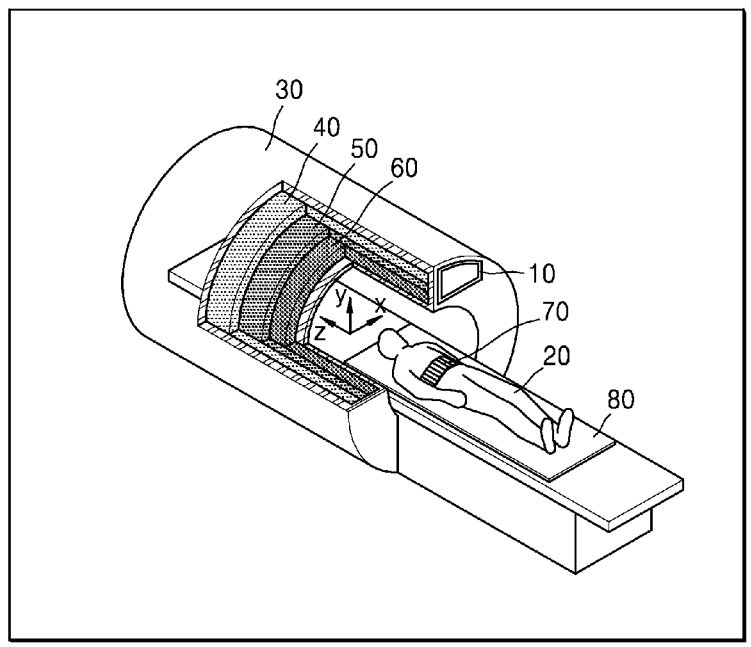
[Fig. 2]
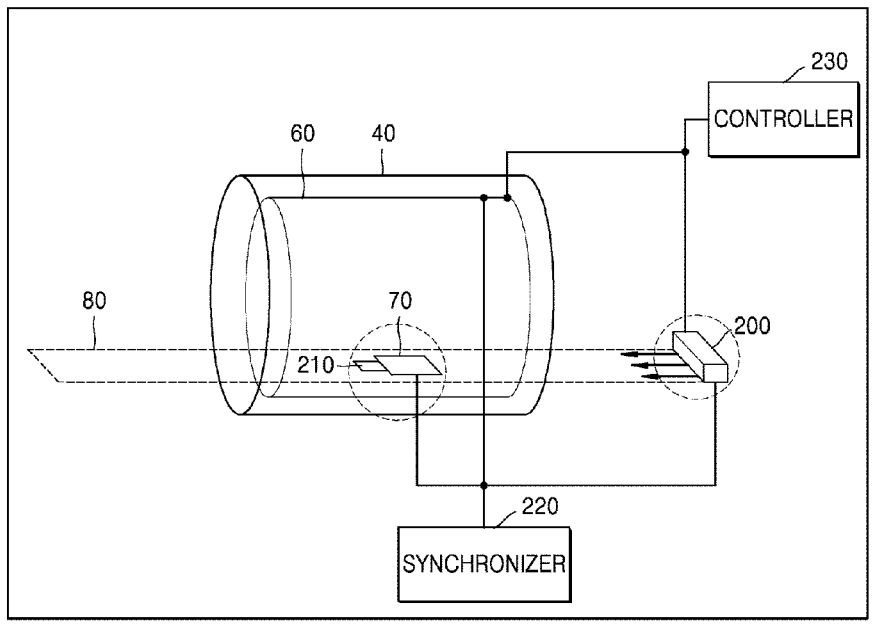

[Fig. 3]
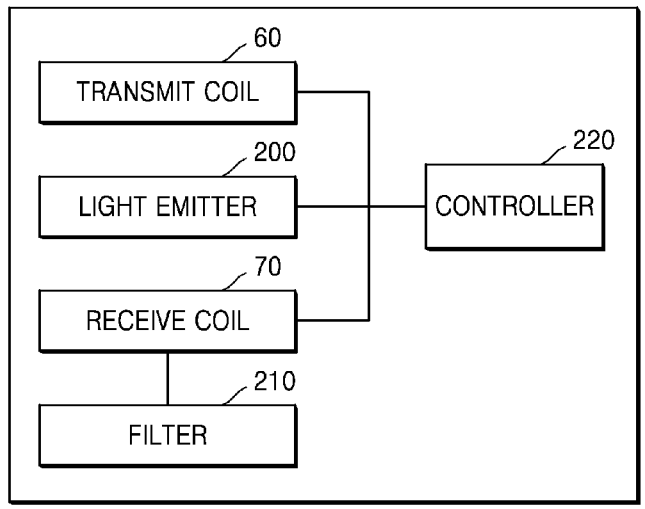
[Fig. 4]
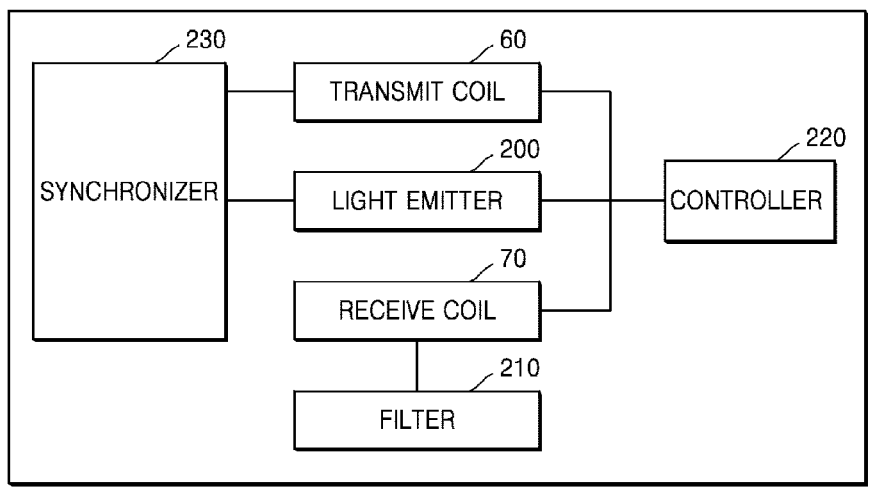
[Fig. 5A]
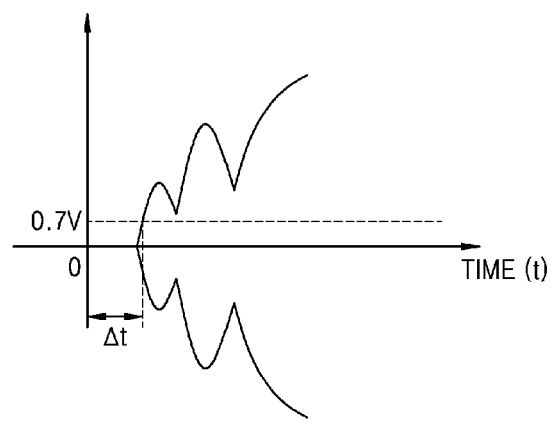

[Fig. 5B]
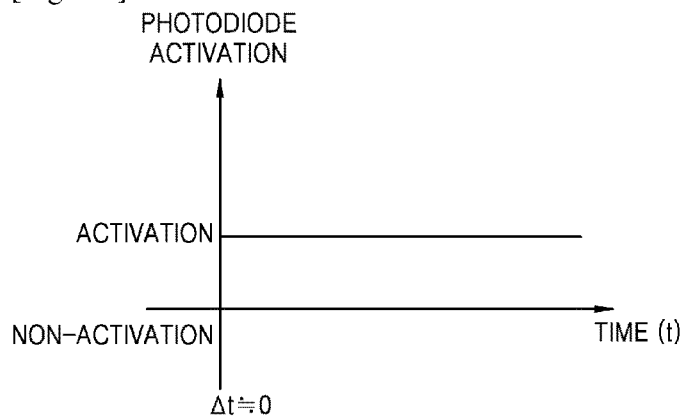
[Fig. 6]
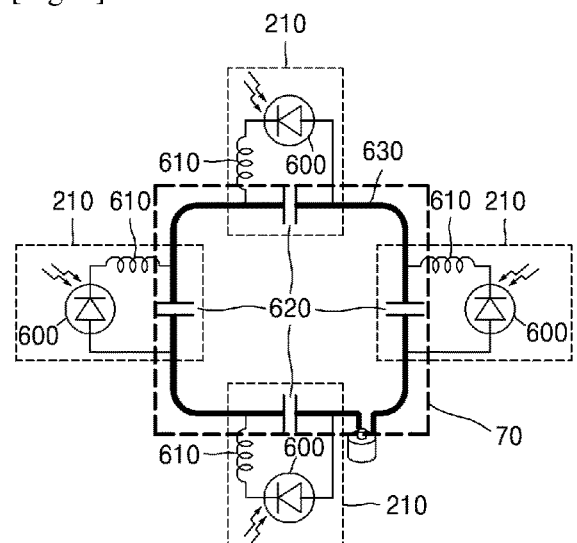
[Fig. 7]
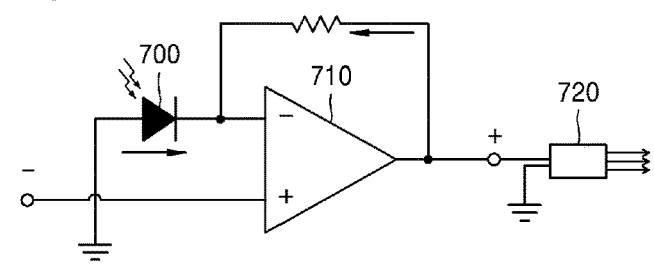
[Fig. 8]
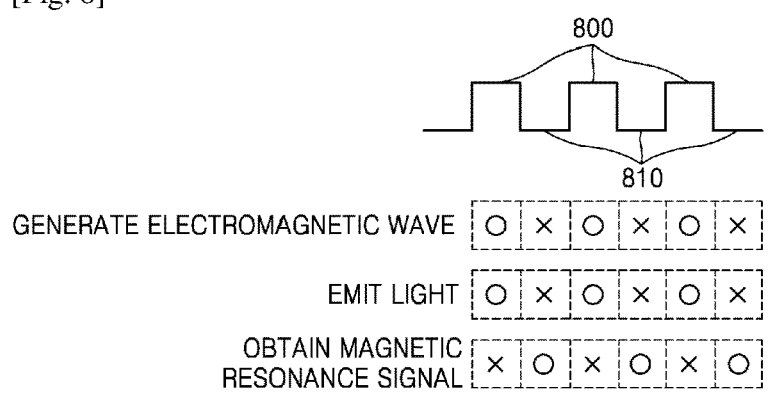

[Fig. 9]
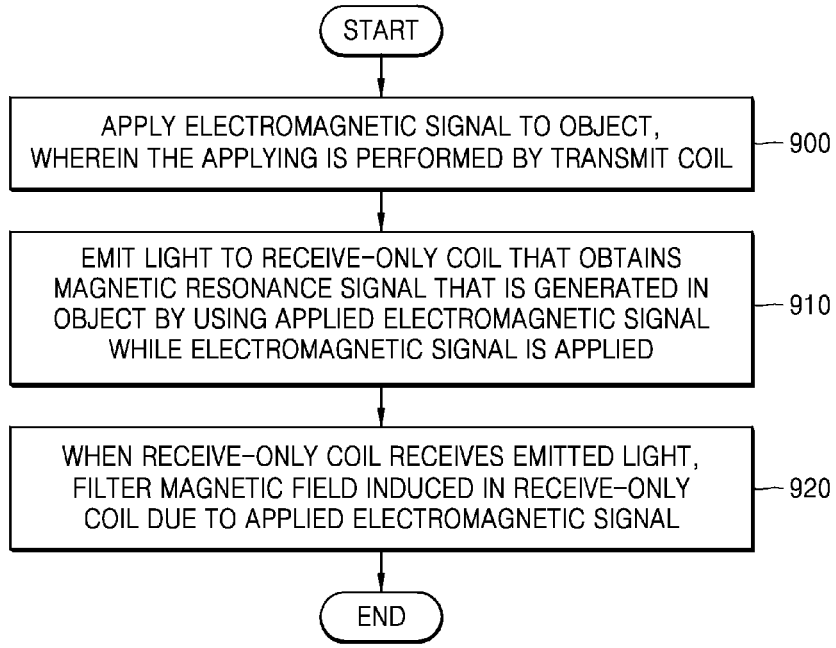
[Fig. 10]
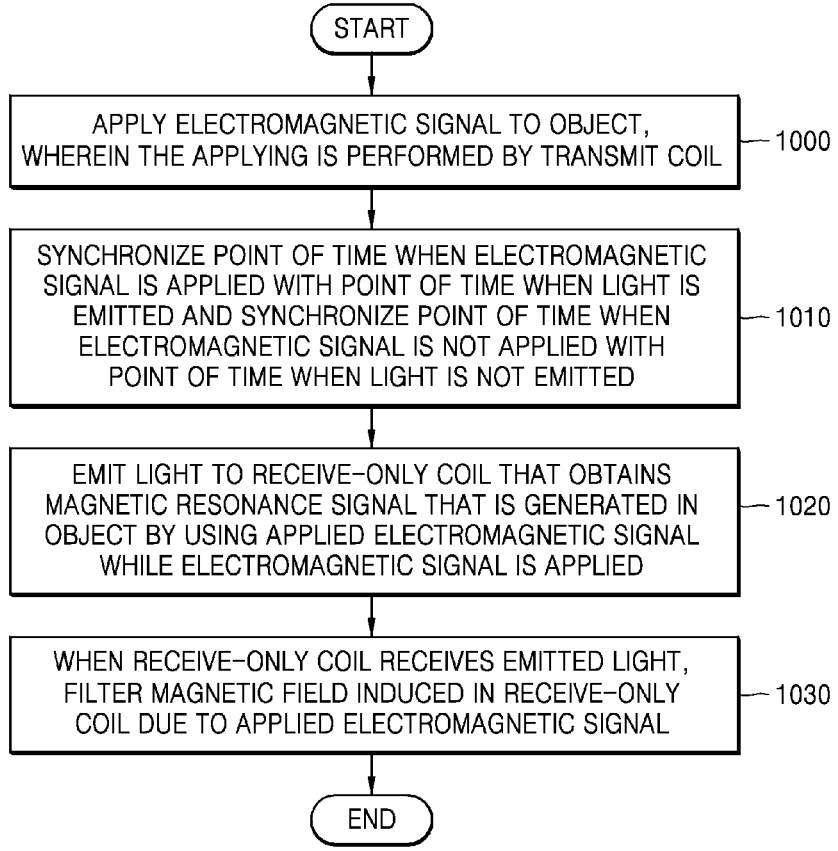

METHOD AND APPARATUS FOR FILTERING MAGNETIC FIELD INDUCED IN COIL OF MRI SYSTEM

CROSS-REFERENCE TO RELATED APPLICATIONS

This application is a U.S. National Stage Application of International Application No. PCT/KR2015/008513, filed on Aug. 13, 2015, which claims the benefit under 35 USC 119(a) and 365(b) of Korean Patent Application No. 10-2014-0105432, filed on Aug. 13, 2014, in the Korean Intellectual Property Office.

TECHNICAL FIELD

The present disclosure relates to methods and apparatuses for filtering a magnetic field induced in a coil of a magnetic resonance imaging (MRI) system.

BACKGROUND ART

A magnetic resonance imaging (MRI) apparatus or a magnetic resonance spectroscopy (MRS) apparatus is a well known magnetic resonance system using nuclear magnetic resonance (NMR).

An MRI apparatus obtains a cross-sectional image of a human body by using NMR. Since atomic nuclei such as hydrogen-1, phosphorus-31, sodium-23, and carbon-13 that are present in the human body have their unique rotating magnetic field constants due to the NMR, the MRI apparatus may obtain the cross-sectional image of the human body by applying a high frequency pulse by using a radio frequency (RF) coil to magnetization vectors of the atomic nuclei that are aligned along an axis of a main magnetic field and allowing the RF coil to receive a magnetic resonance signal that is generated when the magnetization vectors are realigned in a vertical plane due to frequency resonance. However, as a magnetic field is induced in a receive coil due to the RF signal that is transmitted by the RF coil, it is difficult to obtain an accurate result.

DISCLOSURE OF INVENTION

Technical Problem

The present invention relates to a method of controlling a magnetic field of a magnetic resonance imaging (MRI) system. An electromagnetic generator generates an electromagnetic signal, a light emitter emits light toward a magnetic field controller at the same time when the electromagnetic generator generates the electromagnetic signal, and the magnetic field controller that received the light controls an intensity of a magnetic field that is induced in a receive coil due to the generated electromagnetic signal. The magnetic field controller includes a photodiode that receives the light.

Solution to Problem

According to an aspect of the present invention, an apparatus for filtering a magnetic field induced in a coil of a magnetic resonance imaging (MRI) system includes: a transmit coil that applies an electromagnetic signal to an object; a receive-only coil that obtains a magnetic resonance signal that is generated due to the applied electromagnetic signal; a light emitter that emits light towards the receive-only coil while the transmit coil applies the electromagnetic signal; a filter that is connected to the receive-only coil, and upon receiving the emitted light, filters a magnetic field induced in the receive-only coil due to the electromagnetic signal; and a controller that controls operations of the transmit coil, the receive-only coil, and the light emitter.

The apparatus may further include a synchronizer that synchronizes a point of time when the transmit coil applies the electromagnetic signal with a point of time when the light emitter emits the light and synchronizes a point of time when the transmit coil does not apply the electromagnetic signal with a point of time when the light emitter does not emit the light.

The filter may include an inductor and a photodiode that are connected in series, and a capacitor that is connected in parallel to the inductor and the photodiode that are connected in series.

The filter may filter the magnetic field induced in the receive-only coil due to the applied electromagnetic signal when the photodiode receives the light.

The filter may filter the magnetic field induced in the receive-only coil by filtering an electromagnetic signal having a preset frequency band.

The filter may filter the magnetic field induced in the receive-only coil due to the electromagnetic signal such that an intensity of the magnetic field is equal to or less than a preset intensity.

The controller may control the transmit coil and the receive-only coil to repeatedly operate for a preset cycle so that a point of time when the electromagnetic signal is applied and a point of time when the magnetic resonance signal is obtained do not overlap each other.

The light emitter may include an optical device that applies the light and an amplifier that amplifies the light.

The receive-only coil may include a plurality of channel coils, wherein the filter filters the induced magnetic field due to the applied electromagnetic signal for each of the plurality of channel coils.

According to an aspect of the present invention, a method of filtering a magnetic field induced in a coil of a magnetic resonance imaging (MRI) system includes: applying an electromagnetic signal to an object, wherein the applying is performed by a transmit coil; while the electromagnetic signal is applied, emitting light to a receive-only coil that obtains a magnetic resonance signal that is generated in the object due to the applied electromagnetic signal; and when the receive-only coil receives the emitted light, filtering a magnetic field induced in the receive-only coil due to the applied electromagnetic signal.

The method may further include synchronizing a point of time when the electromagnetic signal is applied with a point of time when the light is emitted and synchronizing a point of time when the electromagnetic signal is not applied with a point of time when the light is not emitted.

The filtering may include filtering the magnetic field induced in the receive-only coil by using a circuit that includes an inductor and a photodiode that are connected in series and a capacitor that is connected in parallel to the inductor and the photodiode that are connected in series.

The filtering may include filtering the magnetic field induced in the receive-only coil due to the applied electromagnetic signal when the photodiode receives the light.

The filtering may include filtering the magnetic field induced in the receive-only coil by filtering an electromagnetic signal having a preset frequency band.

The filtering may include filtering the magnetic field induced in the receive-only coil due to the electromagnetic signal such that an intensity of the magnetic wave is equal to or less than a preset intensity.

The transmit coil and the receive-only coil may repeatedly operate for a preset cycle so that a point of time when the electromagnetic signal is applied and a point of time when the magnetic resonance signal is obtained do not overlap each other.

The emitting of the light may include emitting the light by using a circuit that includes an optical device that emits the light and an amplifier that amplifies the light.

The receive-only coil may include a plurality of channel coils, and the filtering may include filtering the induced magnetic field due to the applied electromagnetic signal for each of the plurality of channel coils.

Advantageous Effects of Invention

According to an aspect of the present invention, an apparatus filters a magnetic field induced in a coil of a magnetic resonance imaging (MRI) system

BRIEF DESCRIPTION OF DRAWINGS

These and/or other aspects will become apparent and more readily appreciated from the following description of the embodiments, taken in conjunction with the accompanying drawings in which:

FIG. 1 is a view illustrating a magnetic resonance imaging (MRI) system;

FIG. 2 is a view for explaining an apparatus for filtering a magnetic field induced in a coil of an MRI system, according to an embodiment of the present invention;

FIG. 3 is a block diagram illustrating an apparatus for filtering a magnetic field induced in a coil of an MRI system, according to an embodiment of the present invention;

FIG. 4 is a block diagram illustrating an apparatus for filtering a magnetic field induced in a coil of an MRI system, according to another embodiment of the present invention;

FIGS. 5A and 5B are graphs for explaining the effect of a method of filtering a magnetic field induced in a coil of an MRI system, according to an embodiment of the present invention;

FIG. 6 is a diagram for explaining a receive-only coil of an apparatus for filtering a magnetic field induced in a coil of an MRI system, according to an embodiment of the present invention;

FIG. 7 is a circuit diagram for explaining an apparatus for filtering a magnetic field induced in a coil of an MRI system, according to an embodiment of the present invention;

FIG. 8 is a diagram for explaining an apparatus for controlling a magnetic field in a method of filtering a magnetic field induced in a coil of an MRI system, according to an embodiment of the present invention;

FIG. 9 is a flowchart illustrating a method of filtering a magnetic field induced in a coil of an MRI system, according to an embodiment of the present invention; and FIG. 10 is a flowchart illustrating a method of filtering a magnetic field induced in a coil of an MRI system, according to another embodiment of the present invention.

BEST MODE FOR CARRYING OUT THE INVENTION

As used herein, the term "and/or" includes any and all combinations of one or more of the associated listed items. Expressions such as "at least one of," when preceding a list of elements, modify the entire list of elements and do not modify the individual elements of the list.

The advantages and features of the present invention and methods of achieving the advantages and features will be described more fully with reference to the accompanying drawings, in which exemplary embodiments of the invention are shown. The invention may, however, be embodied in many different forms and should not be construed as being limited to the embodiments set forth herein; rather these embodiments are provided so that this disclosure will be thorough and complete, and will fully convey the concept of the invention to one of ordinary skill in the art. The present invention is only defined by the scope of the appended claims.

Terms used herein will be briefly explained and the present invention will be explained in detail.

Most of the terms used herein are general terms that have been widely used in the technical art to which the present invention pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present invention.

It will be further understood that the terms "comprises" and/or "comprising" used herein specify the presence of stated components, but do not preclude the presence or addition of one or more other components. The term "unit" used herein means a software component or a hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

The present invention will now be described more fully with reference to the accompanying drawings for those of ordinary skill in the art to be able to perform the present invention without any difficulty. Also, parts in the drawings unrelated to the detailed description are omitted to ensure clarity of the present invention.

The term "image" used herein may refer to multi-dimensional data composed of discrete image elements (for example, pixels for two-dimensional (2D) images and voxels for three-dimensional (3D) images).

Also, the term "object" used herein may include a human, an animal, or a body part of a human or an animal. For example, the object may include an organ such as the liver, heart, womb, brain, breast, or stomach, or a blood vessel. Also, the "object" may be a phantom made of a material having a volume very similar to an effective atomic number and a density of a living creature and having properties similar to those of a human body.

Also, the term "user" used herein may refer to, but is not limited to, a medical expert such as a doctor, a nurse, a clinical pathologist, a medical image expert, or an engineer who repairs a medical device.

Also, the term "magnetic resonance image" used herein refers to an image of an object obtained by using nuclear magnetic resonance (NMR).

The term "detuning" used herein refers to an operation of reducing a magnetic field induced in a receive-only coil due to an electromagnetic signal that is generated in a transmit coil while the transmit coil of a magnetic resonance imaging (MRI) system transmits the electromagnetic signal. For example, as the electromagnetic signal that is output from the transmit coil of the MRI system is applied to the receive-only coil of the MRI system, an unnecessary magnetic may be induced in the receive-only coil. The unnecessary magnetic field induced in the receive-only coil may cause mutual inductive coupling between the receive-only coil and the transmit coil, and a resolution of a magnetic resonance image may be reduced due to the mutual inductive coupling. The MRI system may reduce an intensity of the unnecessary magnetic field induced in the receive-only coil by performing detuning.

The term "detuning circuit" used herein may include a circuit for reducing an intensity of a magnetic field induced in a receive-only coil due to an electromagnetic signal that is applied from a transmit coil of an MRI system.

Examples of the detuning circuit may include an active detuning circuit and a passive detuning circuit. The active detuning circuit may be a circuit in which a PIN diode is driven by an external direct current (DC) bias. The passive detuning circuit may be a circuit in which two PIN diodes that act as a switch are driven by a voltage that is induced by the electromagnetic signal that is applied by the transmit coil.

The term "MRI system" refers to a system for obtaining a cross-sectional image of an object by expressing an intensity of a magnetic resonance signal with respect to an electromagnetic signal (e.g., a radio frequency (RF) signal) as a contrast. For example, when an object is placed in a strong magnetic field, an electromagnetic signal that resonates only specific atomic nuclei (for example, hydrogen nuclei) is temporarily emitted to the object and quickly is stopped, a magnetic resonance signal is emitted from the specific atomic nuclei. The MRI system may obtain a magnetic resonance image by receiving the emitted magnetic resonance signal. The magnetic resonance signal is an RF signal that is emitted from the object. A level of the magnetic resonance signal may be determined by, for example, a density of predetermined atoms (e.g., hydrogen) that are included in the object, a relaxation time T1, a relaxation time T2, and a blood flow.

The MRI system has characteristics different from those of other imaging apparatuses. Unlike imaging apparatuses such as a computed tomography (CT) system in which obtaining of an image depends on a direction of detecting hardware, the MRI system may obtain a two-dimensional (2) image or a three-dimensional (3D) volume image that is oriented to an arbitrary point. Also, the MRI system does not expose the object and an investigator to radiation, unlike an X-ray system, a position emission tomography (PET) system, and a single-photon emission computed tomography (SPECT). Also, since the MRI system may obtain an image having a high soft tissue contrast, the MRI system may obtain a neurological image, an intravascular image, a musculoskeletal image, and an oncologic image in which an accurate definition of abnormal tissue is important.

FIG. 1 is a view illustrating an MRI system 1. Referring to FIG. 1, the MRI system 1 may include a display 10, a gantry 30, a main magnet 40, a gradient coil 5, a transmit coil 60, a receive-only coil 70, and a table 80. The gantry 30 may prevent an electromagnetic wave that is generated by the main magnet 40, the gradient coil 50, the transmit coil 60, and the receive-only coil 70 from being radiated to the outside. A static magnetic field and a gradient magnetic field may be formed in a bore of the gantry 30. The MRI system 1 may further include a display 10 that is located inside the gantry 30 in addition to the display 10 that is located outside the gantry 30. The MRI system 1 may provide predetermined information to a user or an object 20 by using the displays that are located inside and outside the gantry 30.

The main magnet 40, the gradient coil 50, the transmit coil 60, and the receive-only coil 70 may be arranged in a predetermined direction of the gantry 30. The predetermined direction may include a coaxial cylindrical direction. The object 20 may be placed on the table 80 that may be inserted into a cylindrical chamber along a horizontal axis.

The main magnet 40 may generate a static magnetic field or a magnetostatic field for aligning directions of magnetic dipole moments of atomic nuclei that are included in the object 20 in a predetermined direction. As a magnetic field that is generated by the main magnet 40 gets stronger and more uniform, a more precise and accurate magnetic resonance image of the object 20 may be obtained.

The gradient coil 50 includes X, Y, and Z coils that apply gradient magnetic fields in X, Y, and Z-axis directions that are perpendicular to one another. The gradient coil 50 may induce different resonance frequencies for different body parts of the object 20 and may provide position information of each of the different body parts of the object 20.

The MRI system 1 may drive the transmit coil 60 or the receive-only coil 70. Also, the MRI system 1 may adjust directions in which an electromagnetic signal and a magnetic resonance signal are transmitted/received. For example, the MRI system 1 may control the transmit coil 60 to apply an electromagnetic signal to the object 20 during a transmission mode and may control the receive-only coil 70 to receive a magnetic resonance signal from the object 20 during a reception mode.

The transmit coil 60 may apply an electromagnetic signal to the object 20 and the receive-only coil 70 may receive a magnetic resonance signal that is emitted from the object 20. In detail, when the transmit coil 60 transmits an electromagnetic signal having the same frequency as a precession frequency to atomic nuclei of the object 20 that precess and stops the transmitting of the electromagnetic signal, the receive-only coil 70 may receive a magnetic resonance signal that is emitted from the object 20.

For example, in order to change atomic nuclei from a low energy state to a high energy state, the transmit coil 60 may generate and apply an electromagnetic signal having an RF, for example, an RF signal, corresponding to a type of the atomic nuclei to the object 20. When the electromagnetic signal that is generated by the transmit coil 60 is applied to the atomic nuclei, the atomic nuclei may be changed from a low energy state to a high energy state. Next, when the electromagnetic signal that is generated by the transmit coil 60 is eliminated, the certain atomic nuclei to which the electromagnetic signal has been applied may be changed from the high energy state to a low energy state, thereby radiating the electromagnetic signal having a Lamor frequency. In other words, when the applying of the electromagnetic signal to the atomic nuclei is stopped, the atomic nuclei to which the electromagnetic signal has been applied is changed from the high energy state to the low energy state, thereby radiating the electromagnetic signal having the Lamor frequency. The receive-only coil 70 may receive the electromagnetic signal that is radiated from atomic nuclei that are included in the object 20. Also, the MRI system 1 may generate MRI data of the object 20 by processing a received magnetic resonance signal.

Also, the transmit coil 60 is fixed to the gantry 30. The receive-only coil 70 may be attachable/detachable. The attachable/detachable receive-only coil 70 may include a receive-only coil for a body part of the object 20, for example, as a head coil, a stomach coil, a leg coil, a neck coil, a shoulder coil, a wrist coil, or an ankle coil. Also, the transmit coil 60 or the receive-only coil 70 may include various channel coils such as 16 channel coils, 32 channel coils, 72 channel coils, or 144 channel coils.

FIG. 2 is a view for explaining an apparatus for filtering a magnetic field induced in a coil of an MRI system 2, according to an embodiment of the present invention. Referring to FIG. 2, the apparatus may include the main magnet 40, the transmit coil 60, the table 80, the receive-only coil 70, a light emitter 200, a filter 210, a controller 220, and a synchronizer 230. The MRI system 2 of FIG. 2 may perform the same function as a function of the MRI system 1 of FIG. 1. For example, the main magnet 40, the transmit coil 60, the table 80, and the receive-only coil 70 of FIG. 2 may perform the same functions as those of the main magnet 40, the transmit coil 60, the table 80, and the receive-only coil 70 of the MRI system 1 of FIG. 1.

The main magnet 40 aligns protons of the object 20 in a direction of a magnetic field. The object 20 may be placed on the table 80. The controller 220 may control operations of the transmit coil 60, the receive-only coil 70, and the light emitter 200. The transmit coil 60 applies an electromagnetic signal. A magnetic field may be induced in the receive-only coil 70 due to the electromagnetic signal that is applied by the transmit coil 60. The synchronizer 230 may synchronize a point of time when the transmit coil 60 applies the electromagnetic signal with a point of time when the light emitter 200 emits light. The light emitter 200 may emit the light to the receive-only coil 70 at a time that is synchronized by the synchronizer 230. When the light emitter 200 emits the light, the filter 210 that is connected to the receive-only coil 70 may filter the magnetic field induced in the receive-only coil 70. An operation of an apparatus for filtering a magnetic field induced in a coil of an MRI system according to an embodiment of the present invention will now be explained in detail with reference to FIGS. 3 and 4.

FIG. 3 is a block diagram illustrating an apparatus 3 for filtering a magnetic field induced in a coil of an MRI system, according to an embodiment of the present invention. The apparatus 3 may include the transmit coil 60, the receive-only coil 70, the light emitter 200, the filter 210, and the controller 220.

The transmit coil 60 may generate an electromagnetic signal. The electromagnetic signal may include a radio frequency corresponding to a type of atomic nuclei in order to change the atomic nuclei from a low energy state to a high energy state. The electromagnetic signal may be applied to the object 20. The transmit coil 60 may include a transmit coil or a transmit-only coil of the MRI system.

The receive-only coil 70 may obtain a magnetic resonance signal that is generated in the object 20 due to the electromagnetic signal. Also, the receive-only coil 70 may obtain the magnetic resonance signal that is generated in a body part of interest of the object 20 that is excited by the electromagnetic signal. The transmit coil 60 and the receive-only coil 70 may repeatedly operate for a preset cycle so that a point of time when the transmit coil 60 applies the electromagnetic signal and a point of time when the receive-only coil 70 obtains the magnetic resonance signal do not overlap each other. For example, when the preset cycle is 2 seconds and the transmit coil 60 may generate the electromagnetic signal for 2 seconds that is a first cycle, the receive-only coil 70 may not obtain the magnetic resonance signal for 2 seconds that is the first cycle. The transmit coil 60 may not apply the electromagnetic signal for 2 seconds that is a second cycle and the receive-only coil 70 may obtain the magnetic resonance signal for 2 seconds that is the second cycle.

The light emitter 200 may emit light to the receive-only coil 70 at the same time as when the transmit coil 60 applies the electromagnetic signal. For example, when the transmit coil 60 applies the electromagnetic signal at, for example, t=0 (sec), the light emitter 200 may emit the light to the receive-only coil 70 at the same time as t=0 (sec). The light emitter 200 may emit the light a photodiode that is included in the filter 210. Also, the light emitter 200 may emit the light to all or some parts of the receive-only coil 70. The light emitter 200 may include an optical device that applies the light and an amplifier that amplifies the light. The light emitter 200 may emit the light to various types of light sources. For example, the light emitter 200 may include a light-emitting diode (LED), a laser, and a tungsten lamp. The light emitter 200 may emit light having various wavelengths. For example, the light emitter 200 may emit light having at least one from among a microwave wavelength, a visible wavelength, an ultraviolet wavelength, and an infrared wavelength. The light emitter 200 will be explained in detail with reference to FIG. 7.

FIG. 7 is a circuit diagram for explaining an apparatus for filtering a magnetic field induced in a coil of an MRI system, according to an embodiment of the present invention. The light emitter 200 may include optical device 700, a light amplifier 710, and a light source 720. The optical device 700 may generate a signal for generating light. For example, the signal for generating the light may include a pulse signal. The light amplifier 710 may amplify a level of the signal that is generated by the optical device 700. The light source 720 may emit light according to the signal that is amplified by the light amplifier 710.

Referring back to FIG. 3, the filter 210 of the apparatus 3 will now be explained. The filter 210 is connected to the receive-only coil 70. When the receive-only coil 70 receives the emitted light, the filter 210 may filter the magnetic field induced in the receive-only coil 70 due to the applied electromagnetic signal. The magnetic field that is filtered by the filter 210 may include a magnetic field induced in the receive-only coil 70. The filter 210 may include at least one photodiode. When the photodiode receives the light that is emitted by the light emitter 200, the filter 210 may filter the magnetic field induced in the receive-only coil 70 due to the applied electromagnetic signal. For example, when the photodiode receives the light that is emitted by the light emitter 200, the photodiode operates. Once the photodiode operates, the filter 210 may operate a band-stop filter and may reduce an intensity of the magnetic field induced in the receive-only coil 70 due to the electromagnetic signal that is applied by the transmit coil 60.

The filter 210 may reduce the intensity of the magnetic field induced in the receive-only coil 70 by filtering an electromagnetic signal having a preset frequency band. The MRI system may use various resonance frequencies. When the MRI system operates at 3 teslas (T), the transmit coil 60 may generate an electromagnetic signal corresponding to a resonant frequency of 127.74 MHz. When the MRI system operates at 4.7 T, the transmit coil 60 may generate an electromagnetic signal corresponding to a resonant frequency of 200 MHz. When the MRI system operates at 7 T, the transmit coil 60 may generate an electromagnetic signal corresponding to a resonant frequency of 300 MHz. When the MRI system operates at 9.4 T, the transmit coil 60 may generate an electromagnetic signal corresponding to a resonant frequency of 400 MHz. Also, the receive-only coil 70 may be set such that a magnetic field is induced by an electromagnetic signal having the same frequency as a resonant frequency of the electromagnetic signal that is applied by the transmit coil 60. For example, when the MRI system 2 operates at 3 T, the preset frequency band may be 127.74 MHz. Accordingly, the filter 210 may reduce the intensity of the magnetic field induced in the receive-only coil 70 by filtering an electromagnetic signal having 127.74 MHz. Also, the filter 210 may include a band-stop filter that filters the electromagnetic signal having 127.74 MHz, and may reduce the intensity of the magnetic field induced in the receive-only coil 70 by using the band-stop filter.

The filter 210 may include an inductor and the photodiode that are connected to each other in series. Also, the filter 210 may include a capacitor that is connected in parallel to the inductor and the photodiode. Since the photodiode of the filter 210 has no directivity, the photodiode may be arranged irrespective of a direction. When the photodiode receives the light that is emitted by the light emitter 200, the photodiode operates and the capacitor that is connected in parallel to the inductor may operate as a band-stop filter. The filter 210 may be connected in series to coils in the receive-only coil 70. The receive-only coil 70 may include a plurality of channel coils. For example, the receive-only coil 70 may include 16 channel coils, 32 channel coils, 72 channel coils, or 144 channel coils. The filter 210 may remove the magnetic field induced by the applied electromagnetic signal for each of the plurality of channel coils.

The filter 210 may control the intensity of the magnetic field induced in the receive-only coil 70 due to the electromagnetic signal such that the intensity of the magnetic field is equal to or less than a preset intensity. For example, the filter 210 may reduce the intensity of the magnetic field induced in the receive-only coil 70 due to the electromagnetic signal to 50 nT that is the preset intensity. Alternatively, the filter 210 may reduce the intensity of the magnetic field induced in the receive-only coil 70 due to the electromagnetic signal to 0T that is the preset intensity. Alternatively, the filter 210 may reduce the intensity of the magnetic field induced in the receive-only coil 70 due to the electromagnetic signal such that the amount of the magnetic field that is reduced corresponds to −30 dB. The filter 210 will now be explained in detail with reference to FIG. 6.

FIG. 6 is a diagram for explaining an apparatus for filtering a magnetic field induced in a coil of an MRI system, according to an embodiment of the present invention. Referring to FIG. 6, the filter 210 may be connected to the receive-only coil 70. Also, a plurality of the filters 210 may be connected to the receive-only coil 70. For example, one receive-only coil 70 may include four filters 210. Also, the receive-only coil 70 may include a plurality of channel coils. The filter 210 may include a photodiode 600 and an inductor 610 that are connected to each other in series. The filter 210 may include a capacitor 620 that is connected in parallel to the photodiode 600 and the inductor 610. The filter 210 may be connected in series to coils 630 in the receive-only coil 70. When the light emitter 200 emits light to the receive-only coil 70, the photodiode 600 of the filter 210 that is connected to the receive-only coil 200 may receive the light. Once the photodiode 600 receives the light, the photodiode 600 may operate and thus the inductor 610 and the capacitor 620 of the filter 210 may be connected to each other in parallel. The inductor 610 and the capacitor 620 that are connected in parallel connected may act as a band-stop filter. When a strength of a magnetic field of the main magnet 40 is 7 T, the MRI system 2 operates at a resonant frequency of 300 MHz. Accordingly, a user may set the filter 210 as a band-stop filter that rejects an electromagnetic signal having a 300 MHz. When the user changes a strength of the main magnet 40, a frequency band that is rejected by the band-stop filter may be changed. Also, the filter 210 using the photodiode 600 may not require external DC power. Also, since a DC power supply is not provided in a coil of the filter 210 that uses the photodiode 600, a DC magnetic field due to the DC power may not be formed, thereby not affecting uniformity of a magnetic field.

Referring back to FIG. 3, the controller 220 of the apparatus 3 will now be explained. The controller 220 may control operations of the transmit coil 60, the receive-only coil 70, and the light emitter 200. The controller 220 may control the transmit coil 60 and the receive-only coil 70 to repeatedly operate for a preset cycle so that a point of time when the transmit coil 60 applies the electromagnetic signal and a point of time when the receive-only coil 70 obtains the magnetic resonance signal do not overlap each other. A method performed by the controller 220 will now be explained in detail with reference to FIG. 8.

FIG. 8 is a diagram for explaining an apparatus for controlling a magnetic field in a method of filtering a magnetic field induced in a coil of an MRI system, according to an embodiment of the present invention. Referring to FIG. 8, operations of the transmit coil 60, the light emitter 200, and the receive-only coil 70 over time will be explained. A time when the light emitter 200 emits light and a time when the receive-only coil 70 obtains a magnetic resonance signal will be explained based on a time 800 when the transmit coil 60 applies an electromagnetic signal and a time 810 when the transmit coil 60 does not apply the electromagnetic signal. A point of time when the transmit coil 60 applies the electromagnetic signal and a point of time when the light emitter 200 emits the light are synchronized with each other by the synchronizer 230. Also, a point of time when the transmit coil 60 does not apply the electromagnetic signal and a point of time when the light emitter 200 does not emit the light are synchronized with each other by the synchronizer 230. Accordingly, it is found that the transmit coil 60 and the light emitter 200 operate at the same time.

However, while receiving the light that is emitted by the light emitter 200, the receive-only coil 70 may not obtain the magnetic resonance signal, and while not receiving the light that is emitted by the light emitter 200, the receive-only coil 70 may obtain the magnetic resonance signal. This is because the magnetic resonance signal is a signal that is generated in the object 20 that receives the electromagnetic signal that is applied by the transmit coil 60 and thus the receive-only coil 70 receives the magnetic resonance signal while the transmit coil 60 does not apply the electromagnetic signal. Accordingly, a point of time when the receive-only coil 70 obtains the magnetic resonance signal does not overlap a point of time when the transmit coil 60 applies the electromagnetic signal or a point of time when the light emitter emits the light.

FIG. 4 is a block diagram for explaining the apparatus 3 according to another embodiment of the present invention.

The apparatus 3 may include the transmit coil 60, the receive-only coil 70, the light emitter 200, the filter 210, and the synchronizer 230. The transmit coil 60, the light emitter 200, and the filter 210 of FIG. 3 may perform the same functions as those of the transmit coil 60, the light emitter 200, and the filter 210 of FIG. 4.

The synchronizer 230 may synchronize a point of time when the transmit coil 60 applies an electromagnetic signal with a point of time when the light emitter 200 emits light and may synchronize a point of time when the transmit coil 60 does not apply the electromagnetic signal with a point of time when the light emitter 200 does not emit the light. For example, the transmit coil 60 may apply the electromagnetic signal from 0 seconds to 10 seconds and may not apply the electromagnetic signal from 10 seconds to 20 seconds. In this case, the synchronizer 230 may enable the light emitter 200 to emit the light from 0 seconds to 10 seconds and not to emit the light from 10 seconds to 20 seconds. Also, the synchronizer 230 may include a magnetic resonance spectrometer (MRS) that measures a time when the transmit coil 600 that generates the electromagnetic signal applies the electromagnetic signal by measuring a signal having a predetermined frequency.

FIGS. 5A and 5B are graphs for explaining the effect of a method of filtering a magnetic field induced in a coil of an MRI system, according to an embodiment of the present invention. Referring to FIG. 5A, a delay time taken for a PIN diode to operate in a passive detuning circuit will now be explained. The passive detuning circuit may include a circuit in which two PIN diodes that act as a switch are driven by a voltage that is induced by an electromagnetic signal that is applied by the transmit coil 60. In the passive detuning circuit, a voltage of each PIN diode that is induced by power of the electromagnetic signal that is applied by the transmit coil 60 may vary according to times. The voltage of the PIN diode may be expressed as a sinc function, and FIG. 5A is a graph obtained by connecting highest points of the sinc function. A point of time (t=0) is a point of time when the transmit coil 60 applies the electromagnetic signal. Since the PIN diode may operate when the voltage of the PIN diode is 0.7 V, the PIN diode does not operate for a delay time of $\Delta t$. Accordingly, the passive detuning circuit may not operate during the delay time of $\Delta t$ beginning from the point of time when the electromagnetic signal is applied. Accordingly, the passive detuning circuit does not filter a magnetic field induced in the receive-only coil 70 due to the electromagnetic signal that is applied by the transmit coil 60 from the point of time when the transmit coil 60 applies the electromagnetic signal till a point of time when the passive detuning circuit operates.

FIG. 5B is a graph for explaining a delay time in a method of filtering a magnetic field induced in a coil of an MRI system, according to an embodiment of the present invention. Referring to FIG. 5B, at t=0, a point of time when the light emitter 200 emits light is synchronized with a point of time when the transmit coil 60 applies an electromagnetic signal. A speed of light is about 3×108 m/s and a time taken for the light that is emitted by the light emitter 200 to reach the receive-only coil 70 is close 0 seconds. The filter 210 that is connected to the receive-only coil 70 may include a photodiode, and the photodiode may receive the light that is emitted by the light emitter 200. Since a response speed of the photodiode is high, a time taken for the photodiode to operate after receiving the light is close to 0 seconds. Accordingly, when a magnetic field induced in the receive-only coil 70 is filtered by using the photodiode, a time taken for the photodiode to operate after receiving the light is close to 0 seconds. Accordingly, in the apparatus 3, a time taken not to filter the magnetic field induced in the receive-only coil 70 due to the electromagnetic signal that is emitted by the transmit coil 60 may be close to 0 seconds.

FIG. 9 is a flowchart illustrating a method of filtering a magnetic field induced in a coil of the MRI system 2, according to an embodiment of the present invention. Referring to FIG. 9, the method includes operations that are sequentially performed by the apparatus 3. Accordingly, even when omitted, the description of the apparatus 3 of FIG. 3 may apply to the method of FIG. 9.

In operation 900, the transmit coil 60 may apply an electromagnetic signal to an object.

In operation 910, light may be emitted to a receive-only coil that obtains a magnetic resonance signal that is generated in the object due to the applied electromagnetic signal by synchronizing a point of time when the electromagnetic signal is applied with a point of time when the light is emitted.

In operation 920, when a filter that is connected to the receive-only coil receives the emitted light, a magnetic field induced in the receive-only coil due to the applied electromagnetic signal may be filtered.

FIG. 10 is a flowchart illustrating a method of filtering a magnetic field induced in a coil of the MRI system 2, according to another embodiment of the present invention. Referring to FIG. 10, the method may include operations that are sequentially performed by the apparatus 3. Accordingly, even when omitted, the description of the apparatus 3 of FIG. 4 may apply to the method of FIG. 10.

In operation 1000, the transmit coil 60 may apply an electromagnetic signal to an object.

In operation 1010, a point of time when the transmit coil 60 applies the electromagnetic signal may be synchronized with a point of time when the light emitter 200 emits light and a point of time when the transmit coil 60 does not apply the electromagnetic signal may be synchronized with a point of time when the light emitter 200 does not emit the light.

In operation 1020, the light may be emitted to the receive-only coil 70 that obtains a magnetic resonance signal that is generated in the object due to the applied electromagnetic signal by synchronizing a point of time when the electromagnetic signal is applied with a point of time when the light is emitted.

In operation 1030, when the receive-only coil 70 that is connected to the filter 210 receives the emitted light, a magnetic field induced in the receive-only coil 70 due to the applied electromagnetic signal may be filtered.

The embodiments of the present invention can be written as computer programs and can be implemented in general-use digital computers that execute the programs using a computer-readable recording medium.

Examples of the computer-readable recording medium include magnetic storage media (e.g., read-only memories (ROMs), floppy disks, or hard disks), optical recording media (e.g., compact disk-ROMs (CD-ROMs), or digital versatile disks (DVDs)), etc.

While the present invention has been particularly shown and described with reference to exemplary embodiments thereof, it will be understood by one of ordinary skill in the art that various changes in form and details may be made therein without departing from the spirit and scope of the present invention as defined by the following claims. Hence, it will be understood that the embodiments described above are not limiting of the scope of the invention.

The invention claimed is:

1. An apparatus for filtering a magnetic field induced in a coil of a magnetic resonance imaging (MRI) system, the apparatus comprising:

a transmit coil configured to apply an electromagnetic signal to an object;

a receive coil configured to obtain a magnetic resonance signal that is generated due to the applied electromagnetic signal;

a light emitter configured to emit light towards the receive coil while the transmit coil applies the electromagnetic signal;

a synchronizer configured to synchronize a point of time at which the transmit coil applies the electromagnetic signal with a point of time at which the light emitter emits the light and configured to synchronize a point of time at which the transmit coil does not apply the electromagnetic signal with a point of time at which the light emitter does not emit the light;

a filter that is connected to the receive coil and configured to, upon receiving the emitted light, filter a magnetic field induced in the receive coil due to the electromagnetic signal; and a controller configured to control operations of the transmit coil, the receive coil, and the light emitter, wherein the synchronizer comprises a magnetic resonance spectrometer (MRS) that measures the point of time at which the transmit coil applies the electromagnetic signal by measuring a signal having a predetermined frequency.

2. The apparatus of claim 1, wherein the filter comprises an inductor and a photodiode that are connected in series, and a capacitor that is connected in parallel to the inductor and the photodiode that are connected in series.

3. The apparatus of claim 2, wherein the filter is further configured to filter the magnetic field induced in the receive coil due to the applied electromagnetic signal in response to the photodiode receiving the light.

4. The apparatus of claim 1, wherein the filter is further configured to filter the magnetic field induced in the receive coil by filtering an electromagnetic signal having a preset frequency band.

5. The apparatus of claim 1, wherein the filter is further configured to filter the magnetic field induced in the receive coil due to the electromagnetic signal such that an intensity of the magnetic field is equal to or less than a preset intensity.

6. The apparatus of claim 1, wherein the controller is further configured to control the transmit coil and the receive coil to repeatedly operate for a preset cycle so that the point of time at which the electromagnetic signal is applied and a point of time at which the magnetic resonance signal is obtained do not overlap each other.

7. The apparatus of claim 1, wherein the light emitter is configured to emit the light based on a signal received from an optical device, the signal being amplified by an amplifier.

8. The apparatus of claim 1, wherein the receive coil comprises a plurality of channel coils, wherein the filter is further configured to filter the induced magnetic field due to the applied electromagnetic signal for each of the plurality of channel coils.

9. A method of filtering a magnetic field induced in a coil of a magnetic resonance imaging (MRI) system, the method comprising:

applying an electromagnetic signal to an object, wherein the applying is performed by a transmit coil;

while the electromagnetic signal is applied, emitting light to a receive coil that obtains a magnetic resonance signal that is generated in the object due to the applied electromagnetic signal;

in response to the receive coil receiving the emitted light, filtering a magnetic field induced in the receive coil due to the applied electromagnetic signal; and synchronizing a point of time at which the electromagnetic signal is applied with a point of time at which the light is emitted and synchronizing a point of time at which the electromagnetic signal is not applied with a point of time at which the light is not emitted, wherein the method further comprises measuring, by a magnetic resonance spectrometer (MRS), the point of time at which the transmit coil applies the electromagnetic signal by measuring a signal having a predetermined frequency.

10. The method of claim 9, wherein the filtering comprises filtering the magnetic field induced in the receive coil by using a circuit that comprises an inductor and a photodiode that are connected in series and a capacitor that is connected in parallel to the inductor and the photodiode that are connected in series.

11. The method of claim 10, wherein the filtering comprises filtering the magnetic field induced in the receive coil due to the applied electromagnetic signal in response to the photodiode receiving the light.

12. The method of claim 9, wherein the filtering comprises filtering the magnetic field induced in the receive coil by filtering an electromagnetic signal having a preset frequency band.

13. The method of claim 9, wherein the filtering comprises filtering the magnetic field induced in the receive coil due to the electromagnetic signal such that an intensity of the magnetic wave is equal to or less than a preset intensity.

14. The method of claim 9, wherein the transmit coil and the receive coil repeatedly operate for a preset cycle so that the point of time at which the electromagnetic signal is applied and a point of time at which the magnetic resonance signal is obtained do not overlap each other.

15. The method of claim 9, wherein the emitting of the light is performed by a light emitter based on a signal received from an optical device, the signal being amplified by an amplifier.

16. The method of claim 9, wherein the receive coil comprises a plurality of channel coils, and the filtering comprises filtering the induced magnetic field due to the applied electromagnetic signal for each of the plurality of channel coils.

17. A non-transitory computer-readable storage medium storing instructions, that when executed by a processor, cause the processor to perform the method of claim 9.

18. An apparatus for filtering a magnetic field induced in a coil of a magnetic resonance imaging (MRI) system, the apparatus comprising:

a transmit coil configured to apply an electromagnetic signal to an object;

a receive coil configured to obtain a magnetic resonance signal that is generated due to the applied electromagnetic signal, wherein the receive coil comprises a plurality of channel coils;

a light emitter configured to light towards the receive coil while the transmit coil applies the electromagnetic signal;

a synchronizer configured to synchronize a point of time at which the transmit coil applies the electromagnetic signal with a point of time at which the ligh emitter emits the light and configured to synchronize a point of time at which the transmit coil does not apply the electromagnetic signal with a point of time at which the light emitter does not emit the light;

a filter that is connected to the receive coil and configured to, upon receiving the emitted light, filter a magnetic field induced in the receive coil due to the electromagnetic signal for each of the plurality of channel coils; and a controller configured to control operations of the transmit coil, the receive coil, and the light emitter, wherein the synchronizer comprises a magnetic resonance spectrometer (MRS) that measures the point of time at which the transmit coil applies the electromagnetic signal by measuring a signal having a predetermined frequency.

\* \* \* \* \*